(12) United States Patent
Takimoto et al.

(10) Patent No.: US 8,602,559 B2
(45) Date of Patent: Dec. 10, 2013

(54) PERIMETER

(75) Inventors: Shigeru Takimoto, Shizuoka-Ken (JP);
Satoshi Shimada, Shizuoka-Ken (JP);
Masayoshi Oouchi, Shizuoka-Ken (JP)

(73) Assignee: Kowa Company, Ltd., Aichi-Ken (JP)

( * ) Notice: Subject to any disclaimer, the term of this patent is extended or adjusted under 35 U.S.C. 154(b) by 0 days.

(21) Appl. No.: 13/351,352

(22) Filed: Jan. 17, 2012

(65) Prior Publication Data
US 2012/0224144 A1 Sep. 6, 2012

(30) Foreign Application Priority Data

Mar. 4, 2011 (JP) .................................. 2011-047352

(51) Int. Cl.
*A61B 3/02* (2006.01)

(52) U.S. Cl.
USPC .......................................................... 351/224

(58) Field of Classification Search
USPC .................. 351/224, 206, 237, 211
See application file for complete search history.

(56) References Cited

U.S. PATENT DOCUMENTS

| | | | |
|---|---|---|---|
| 5,220,361 A | 6/1993 | Lehmer et al. | |
| 2004/0057013 A1* | 3/2004 | Cappo et al. | 351/224 |
| 2009/0109399 A1* | 4/2009 | Severns | 351/210 |

FOREIGN PATENT DOCUMENTS

| | | |
|---|---|---|
| JP | 62 9330 | 2/1987 |
| JP | 6 16748 | 3/1994 |
| JP | 164425 | 6/2003 |
| JP | .088541 | 4/2010 |

* cited by examiner

Primary Examiner — Scott J Sugarman
Assistant Examiner — Mustak Choudhury
(74) Attorney, Agent, or Firm — Law Offices of Robert F. Zielinski

(57) ABSTRACT

In a perimeter having means for measuring a visual field of an eye to be examined, means for monitoring fixation state and means for lighting the eye to be examined with a brightness necessary for monitoring the fixation state of the eye to be examined and means for correcting visibility, means for correcting visibility is provided so as to be freely moved between a set position corresponding to a measurement position of the eye to be examined and a stored position retracted to an outer periphery of a projection member. Such a perimeter further has means for detecting whether means for correcting visibility is at the set position or the stored position and an illustration controller for changing brightness of the illumination onto the eye to be examined through the means for lighting according to the detected position of means for correcting visibility.

5 Claims, 10 Drawing Sheets

PERIMETER

CROSS REFERENCE TO RELATED APPLICATION

The present disclosure relates to subject matter contained in Japanese patent application No. 2011-047352 filed on Mar. 4, 2011, the disclosure of which is expressly incorporated herein by reference in its entirety.

BACKGROUND OF THE INVENTION

The invention relates to a perimeter for measuring a visual field (perimetry), and especially relates to a perimeter having a visibility corrector, such as a lens holder, to which a correction lens is attachable.

A perimeter with a mechanism for locating visibility corrector, such as a lens for correcting the visibility of an eye to be examined, has been known, as disclosed in Patent related document 1 mentioned hereinafter.

Perimetry takes a longer time, and a fixation state of an eye to be examined may be shifted during the perimetry. In such a state, it is not possible to obtain a correct measurement result. For this reason, a fixation state monitor for detecting whether the fixation state of the eye to be examined is stable has been proposed as disclosed in Patent related documents 1 and 2 mentioned hereinafter. Furthermore, Patent related documents 4 discloses such an art that credibility of the measurement value is judged and such a judgment is set as a standard at a time of reexamination.

PRIOR ART

Patent related document 1: Japanese Laid-open Patent Publication No. 2003-164425.
Patent related document 2: Japanese Examined Patent Publication No. S62-009330.
Patent related document 3: Japanese Examined Patent Publication No. H06-16748.
Patent related document 4: Japanese Laid-open Patent Publication NO. 2010-088541.

Problems to be Solved by Invention

It is desirable to provide the visibility corrector, such as a mechanism in which a lens for correcting the visibility is located, and the fixation state monitor for judging credibility of the measurement result together in the same perimeter. If both are simply provided, an auxiliary lens or the lens holder that supports the auxiliary lens is located between a front eye portion of the eye to be examined and ion a fixation state monitor for watching the fixation state. Then, due to light emitted from a light source for watching the fixation that is located for detecting the fixation state to the front eye portion, a shadow of the auxiliary lend and/or the lens holder is projected to the front eye portion. Such a shadow prevents watching of the fixation state and it is not possible to correctly detect the fixation state.

Then, an object of the invention is to provide the perimeter for correctly detect the fixation state without being obstructing by the auxiliary lens or the lens holder supporting the auxiliary lens even if the mechanism for locating the lens for correcting the visibility and the fixation state monitor for detecting the fixation state and judging credibility of a measured value are located at the same perimeter.

Means for Solving Problems

A first aspect for solving the above-mentioned problems is a perimeter (1) having:

a visual field measurer (26, 27) that measures a visual field of an eye to be examined (19) when the eye to be examined (19) perceives stimuli (16) projected in order at different positions on a projection member (15);

a fixation state monitor (18) that monitors a fixation state of the eye to be examined at a time of perimetry;

said fixation state monitor having an illuminator (20, 21, 22) that lights the eye to be examined at a brightness necessary for monitoring the fixation state of the eye to be examined; and a visibility corrector (7) that corrects visibility of the eye to be examined; said perimeter (1) further comprising:

said visibility corrector (7) being provided so as to be freely moved between a set position (P1) corresponding to a measurement position (CT) of the eye to be examined and a stored position (P2) retracted to an outer periphery (15b) of a projection member with respect to the projection member (15);

a position detector (13) that detects whether said visibility corrector is positioned at said set position or said stored position;

an illumination controller (29) that changes brightness of lighting onto the eye to be examined through said illuminator according to a position of said visibility corrector detected by said position detector (13).

A second aspect for solving the above-mentioned problems is the perimeter, wherein said illuminator is comprised of two or more light sources (20, 21, 22) respectively located at different positions, and said illumination controller controls to light the eye to be examined (19) by more light sources (20, 21, 22) rather than a case where said visibility corrector (7) is positioned at said stored position (P2) when said visibility corrector (7) is positioned at said set position (P1).

A third aspect for solving the above-mentioned problems is the perimeter, wherein said illuminator has at least two light sources, at least one of said light sources is positioned at a position where the eye to be examined can be lighted via a lens for correcting visibility that is held by said visibility corrector when said visibility corrector is used at said set position;

at least the other one light source is positioned at a position where the eye to be examined can be directly lighted without passing through said lens for correcting visibility that is held by said visibility corrector even if said visibility corrector is used at said set position.

A fourth aspect for solving the above-mentioned problems is the perimeter, wherein said illuminator has at least three light sources (20, 21, 22), and at least one of said light sources is located on a lower hand of a center of said projection member and at least two light sources are positioned at both sides of a lower hand of said projection member.

Effects of Invention

According to the first aspect for solving the above-mentioned problems, the illumination controller (29) is able to change the brightness onto the eye to be examined (19) through the illuminator (20, 21, 22) according to the position of the visibility corrector (7) detected by the position detector (13), so that it is possible to correctly detect the fixation state without being hindered by the visibility corrector even if the lens for correcting visibility and the mechanism for locating the lens, that is, the visibility corrector (7) and the fixation state detector are located at the same perimeter.

According to the second aspect for solving the above-mentioned problems, the illumination controller controls to light the eye to be examined (19) by more light sources (20, 21, 22) rather than a case where the visibility corrector (7) is positioned at the stored position (P2) if the visibility corrector (7) is positioned at the set position (P1), so that lighting is possible so as to cancel the shadow of the visibility corrector projected to the front eye portion due to some light source by the other light source and it is possible to light the eye to be examined (19) in a uniform state with little shadows and to more smoothly monitor the eye to be examined (19) through the fixation state monitor (18).

According to the third aspect for solving the above-mentioned problems, the eye to be examined is lighted by at least one illuminator through the lens for correcting visibility that is held by the visibility corrector and the eye to be examined is directly lighted by at least one remaining illuminator without passing through the lens for correcting visibility when the visibility corrector is used at the set position, so that it is possible to extremely prevent the shadow of the visibility corrector from being projected onto the eye to be examined.

According to the fourth aspect for solving the above-mentioned problems, the illuminator has at least three light sources (20, 21, 22), and at least one of the light sources is located on a lower hand of a center of the projection member and at least two light sources are positioned at both sides of a lower hand of the projection member, so that the light is emitted onto the eye to be examined (19) from at least three directions different from each other, and the shadow of the visibility corrector thrown onto the front eye portion of the eye to be examined (19) is cancelled and the fixation state monitor 18 is able to properly monitor the fixation state of the eye to be examined (19). Besides, the light sources (20, 21, 22) are located on the lower side of the projection member (15), that is, on the lower hand of the perimetry position (corresponding to the center CT) in the projection member (15) of the eye to be examined (19), so that it is possible to light the eye to be examined (19) through the light sources (20, 21 and 22) without being hindered by a forehead portion that is on the upper portion of the eye to be examined (19).

The number in parentheses shows the corresponding element in the drawings for the sake of convenience, accordingly, the descriptions are not restricted and bound by the descriptions on the drawings.

PREFERRED EMBODIMENT

An embodiment of the invention is now explained, referring to appended drawings.

Figure 1:
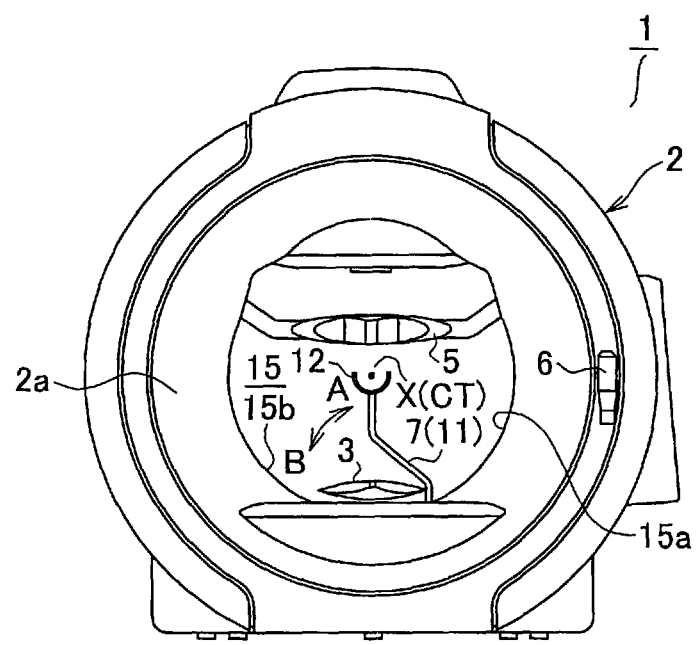
FIG. 1 is a front view that shows an example of a perimeter to which the invention is applied.
Figure 2:
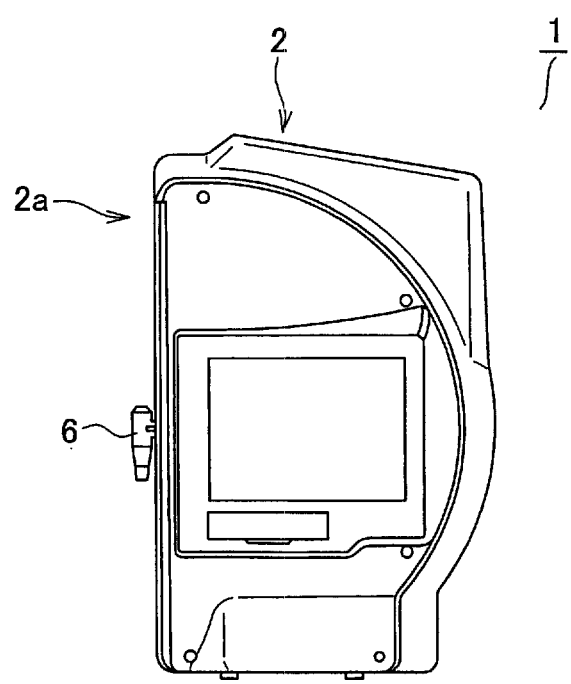
FIG. 2 is a side view of FIG. 1.
Figure 3:
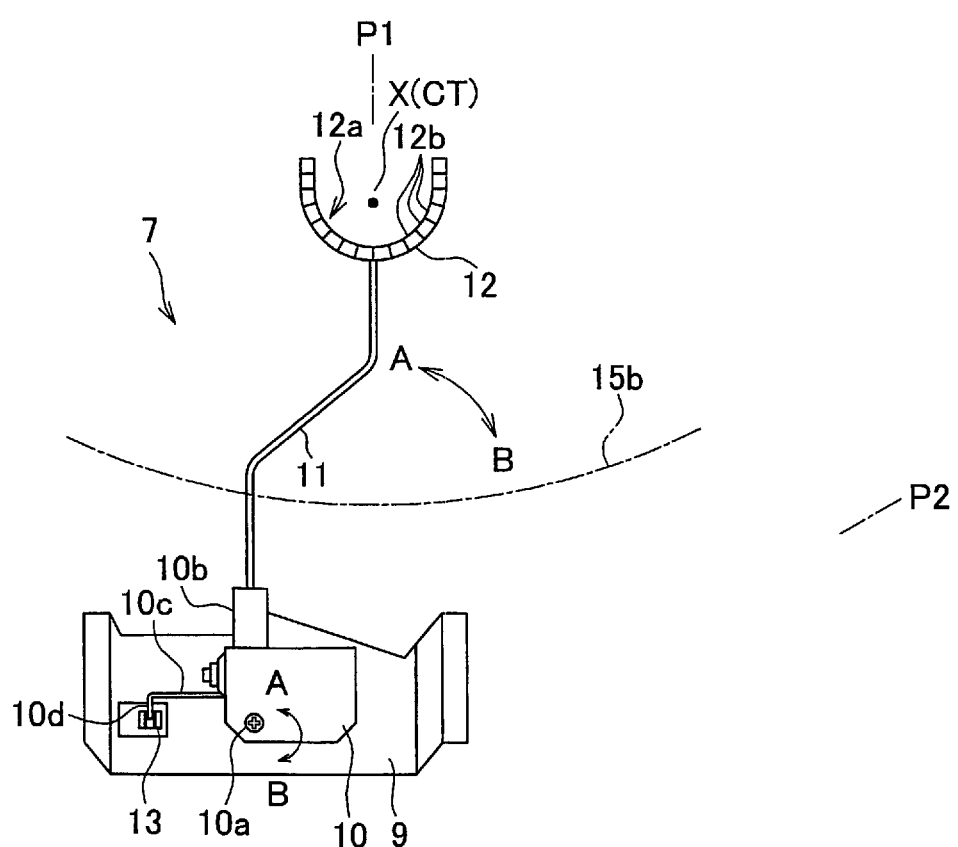
FIG. 3 is a front view that shows an example of a lens holder to be installed in the perimeter of FIG. 1.

As shown in FIGS. 1 and 2, a perimeter 1 has a main body 2 the whole of which is in the shape of a box, and a jaw stand 3 and a forehead pad 5 are provided at a front face 2a of the main body 2. A response switch 6 is attachably and detachably located on a right side of FIG. 1 of the main body 2, and a lens holder 7 is provided at a back of the paper of FIG. 1 of the jaw stand 3. As shown in FIG. 3, the lens holder 7 has a bracket 9 that is attached to the main body 2, and a holder body 10 is provided at the bracket 9 so as to go and return in a direction as shown by arrows A and B between a set position P1 and a stored position P2 as shown in FIG. 3 with a rotation axis 10a as its center.

Figure 5:
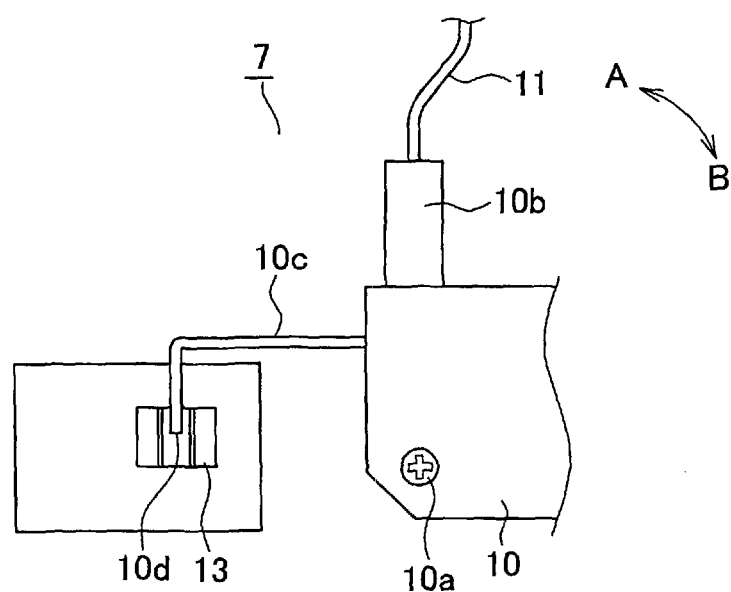
FIG. 5 is an enlarged view of a sensor of the lens holder of FIG. 3.
Figure 6:
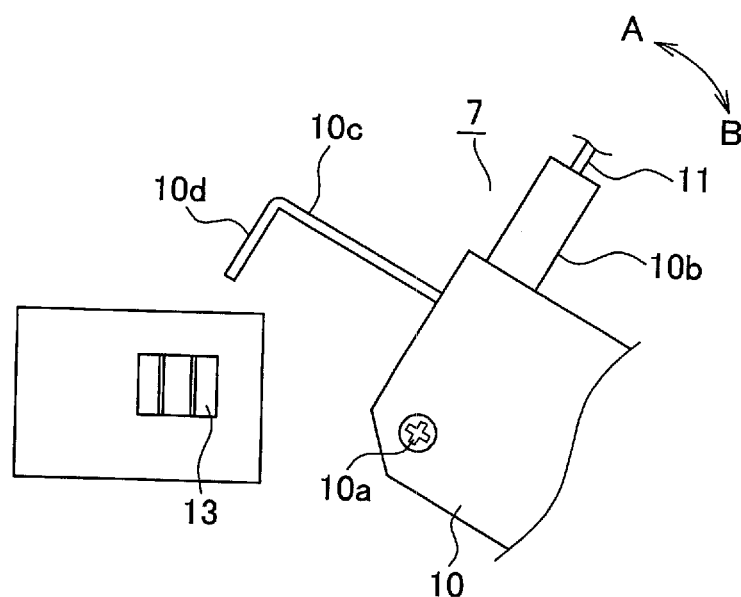
FIG. 6 is an enlarged view of the sensor of the lens holder of FIG. 4.

A stem 11 is installed on the holder body 10 through an axial portion 10b that is provided so as to be moved and positioned in a direction perpendicular to the paper of FIGS. 1 and 3, that is, in a direction parallel to an optical axis X direction of a correction lens installed on a lens holder portion 12 mentioned hereinafter (in a direction as shown by arrows C and D of FIG. 8), and the lens holder portion 12 is formed at a top end of the stem 11. And, a concave portion 12a is provided at a top end of the lens holder portion 12. A correction lens for correcting visibility of an eye to be examined (not shown) is exchangeably installed in the concave portion 12a, and in a case where the correction lens is one for astigmatism correction, an angle index 12b for adjusting its set angle is provided at the lens holder portion 12. A probe 10c formed in the shape of L character is provided at a left side of FIG. 3 of the holder body 10 such that a bent top end 10d is able to be inserted in and pulled out of a lens holder sensor 13 provided at the bracket 9 with a rotation of the lens holder portion 12 in the direction as shown by the arrows A and B, and the lens holder sensor 13 outputs an ON ("1") signal when the top end 10d of the probe 10c is inserted into the lens holder sensor 13 as shown in FIG. 5 and outputs an OFF ("0") signal when the top end 10d is pulled out of the lens holder sensor 13 as shown in FIG. 6.

Figure 7:
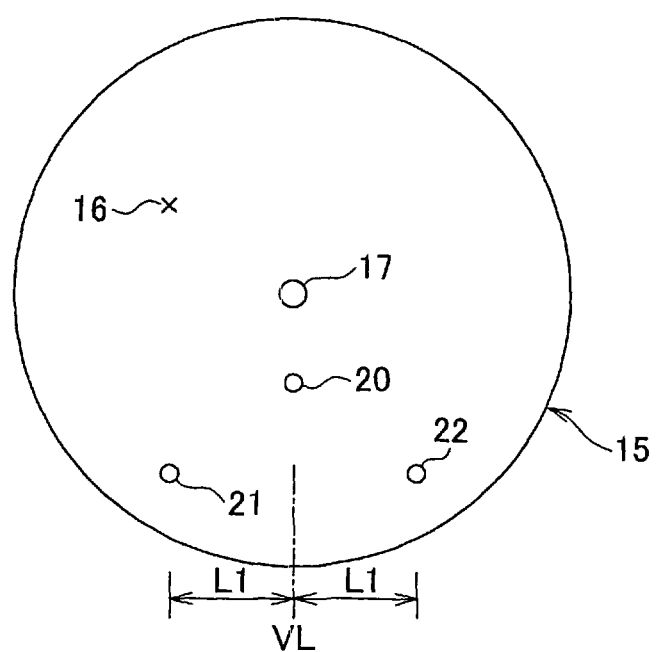
FIG. 7 is a front view that shows projection members of the perimeter of FIG. 1, such as a visual field dome.
Figure 8:
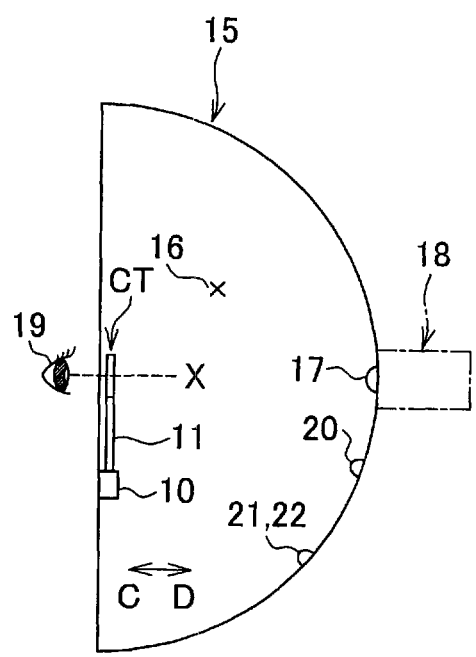
FIG. 8 is a side view of FIG. 7.

In the main body 2 of a back of the paper of FIG. 1 of the lens holder 7, projection members, such as a visual field dome 15 in a semi-spherical shape through which stimuli are presented, are provided, and as shown in FIGS. 7 and 8, a stimulus 16 for perimetry can be presented at an optional position in the visual field dome 15 through a well-known stimulus presenter mentioned hereinafter. A fixation lamp 17 that is a target when an eye to be examined fixates is provided at an innermost portion of the dome 15 with respect to the front face 2a of the man body in the visual field dome 15, and a well-known fixation state monitor 18 for watching a fixation state of an eye to be examined 19 is provided at the back of FIG. 7 of the fixation lamp 17, that is, on a right hand of FIG. 8 such that the fixation state of the eye to be examined 19 can be monitored at the time of perimetry.

Three LED illuminations 20, 21 and 22 are located on a lower hand of FIG. 7 of the fixation lamp 17 of the visual field dome 15, that is, on the visual field dome 15 on an obliquely lower hand of FIG. 8 of the eye to be examined 19. The LED illumination 20 is located on a lower hand in the vertical direction of the fixation lamp 17 that is a center position (that is, the lower hand of the center portion of the visual filed dome 15), and the remaining two LED illuminations 21 and 22 are located at symmetrical positions in a right/left direction with respect to a vertical face VL passing the fixation lamp 17 and the LED illumination 20 on the lower hand of the fixation lamp 17 (that is, both sides of the lower hand of the visual field dome 15) such that each of both symmetrical positions is apart from the vertical face VL by a predetermined distance L1.

Figure 9:
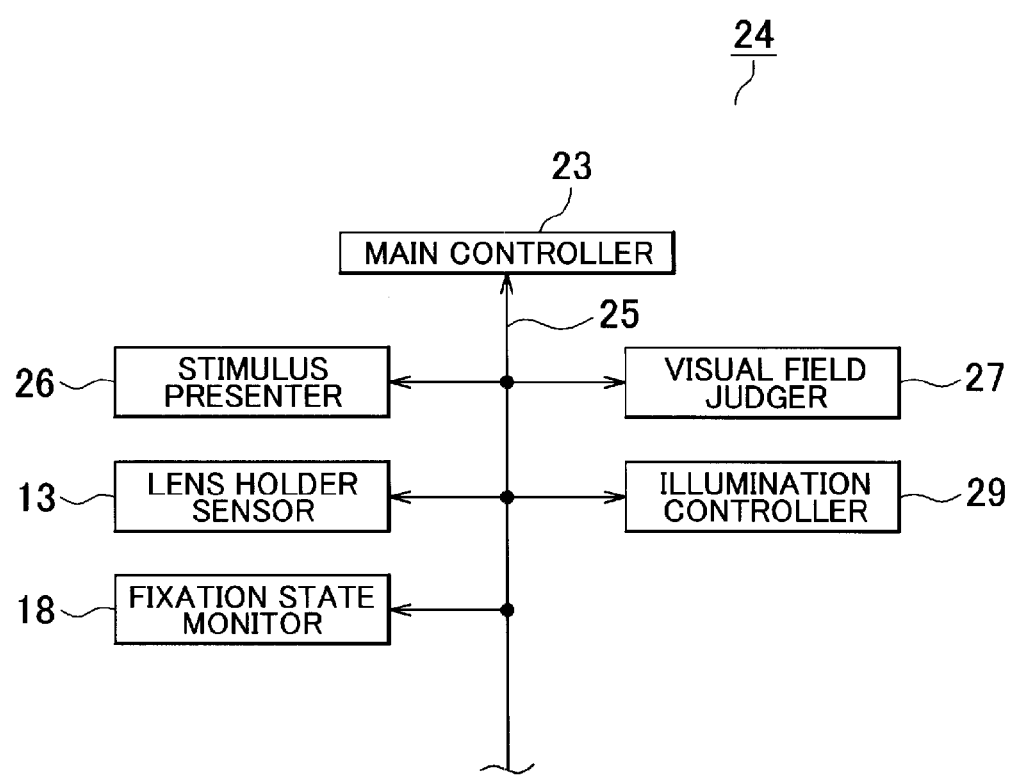
FIG. 9 is a control block diagram of the perimeter of FIG. 1.

As shown in FIG. 9, a controller 24 of the perimeter is provided at the main body 2 of the perimeter 1, and the controller 24 has a main controller 23. A stimulus presenter 26, a visual field judger 27, the above-mentioned lens holder sensor 13, an illumination controller 29 and the fixation state monitor 18 are connected with the main controller 23 via a bus line 25. A control block diagram as shown in FIG. 9 shows only portions pertinent to the invention and the other structural portions having no connection are not shown.

Figure 4:
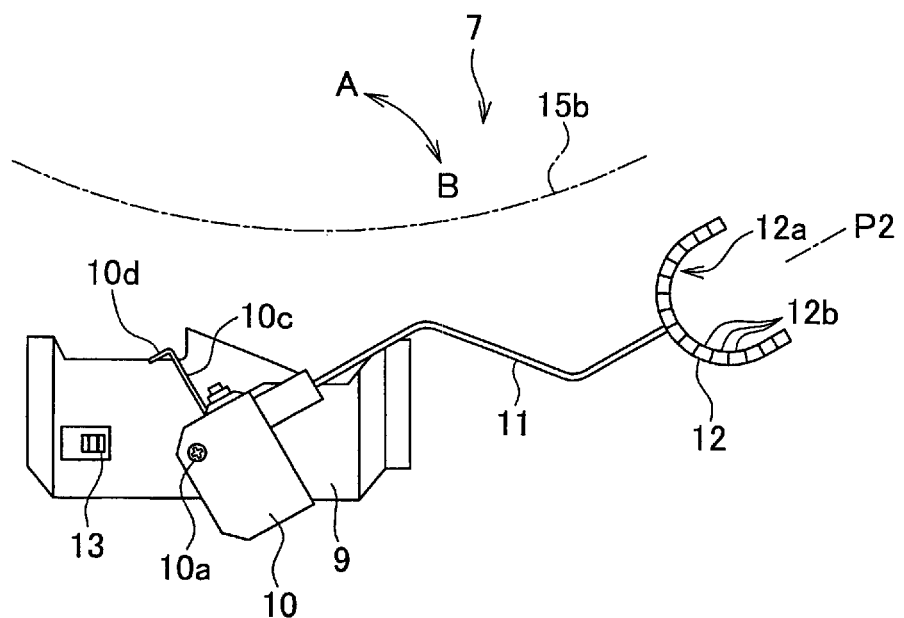
FIG. 4 is a front view that shows a laid down state of a holder body of the lens holder of FIG. 3.

The perimeter 1 has the above-mentioned structure. In a case where the visual field of the eye to be examined 19 is measured and it is not necessary to adjust the visibility of the eye to be examined 19, an examiner rotates the lens holder 7 in the arrow B direction with the rotation axis 10a as its center as shown in FIG. 4 so as to position the stem 11 and the lens holder portion 12 at the stored position P2. Then, the stem 11 and the lens holder portion 12 are rotated and moved in the arrow B direction from the front face portion as shown in FIG. 1 of the perimeter 1, and such a last state that the lens holder portion 12 is located at the set position P1 of the center portion of an opening 15a of the visual field dome 15 (see FIG. 3), that is, a position corresponding to a measurement position (almost central position of the visual field dome 15) of the eye to be examined where the eye to be examined 19 is located at the time of perimetry is changed into such a state that the stem 11 and the lens holder portion 12 are retracted and stored at the stored position P2 of the lower hand of an outer periphery 15b of the front face of FIG. 1 of the opening 15a (see FIG. 4), and in such a state, the stem 11 and the lens holder portion 12 are not present (are not watched) at the opening 15a as shown in FIG. 1 having almost circular shape when viewing from the direction perpendicular to the paper of FIG. 1.

In the afore-mentioned state, an examinee is invited to put his (her) jaw on the jaw stand 3 and contact his (her) forehead with the forehead pad 5 so as to be pressed against such a pad such that the eye to be examined 19 of a front eye portion of the examinee is located at a predetermined perimetry position, that is, at an almost central position CT of the visual field dome 15 as shown in FIG. 8. If the perimeter 1 is instructed to start perimetry of the eye to be examined 19 through an operation portion, such as a keyboard (not shown) in the afore-mentioned state, the main controller 23 of the controller 24 presents stimuli 16 in order at proper positions in the visual field dome 15 through the stimulus presenter 26 with a well-known method. If the examinee perceives the presented stimulus through the eye to be examined 19, the examinee operates the response switch 6 and if not, no operation of the response switch 6 is done. The visual field judger 27 measures the visual field of the eye to be examined with a well-known method, relating the operation state of the response switch 6 and the stimulus position at such a time with each other.

On this occasion, in order to properly conduct the perimetry the main controller 23 gets the fixation state monitor 18 to watch whether the eye to be examined 19 always fixates the fixation lamp 17 during the perimetry, that is, whether the fixation state is maintained. Such a method of watching the fixation state is already well known, so its detailed explanation is not mentioned. At a time of monitoring the fixation state, the main controller 23 drives the three LED illuminations 20, 21 and 22 through the illumination controller 29 in order to properly monitor the fixation state by the fixation state monitor 18 and controls to such a driving state such that the eye to be examined 19 on which the perimetry is conducted can receive light having brightness proper for the fixation state monitoring for watching whether the eye to be examined 19 is in the fixation state necessary for the perimetry.

That is to say, the illumination controller 29 monitors an output state of the lens holder sensor 13, and if the output of the lens holder sensor 13 is an OFF signal, that is, the lens holder portion 12 of the lens holder 7 is stored in the stored position P2 as shown in FIG. 4, the LED illumination 20 that is in a center of FIG. 7 is driven with low brightness and the LED illuminations 21 and 22 of both sides are not driven. Then, the eye to be examined 19 is lighted by only LED illumination 20 on the vertically lower hand of the fixation lamp 17 with low brightness. As already mentioned, the lens holder portion 12 is at the stored position P2 that is stored at the back of the front face 2a of the main body on the lower hand of the periphery 15b of the visual field dome 15 of FIG. 1 together with the stem 11. For this reason, the lens holder 7 is not a hindrance of monitoring of the fixation state monitor 18, and it is possible to sufficiently monitor the fixation state of the eye to be examined 19 even with the lighting of the LED illumination 20 which emission is controlled at low brightness.

In a case where it is necessary to adjust the visibility of the eye to be examined 19, the examiner rotates the lens holder 7 in the arrow A direction with the rotation axis 10a as its center as shown in FIG. 3 so as to position the stem 11 and the lens holder portion 12 from the last stored position P2 to the set position P1. Then, the lens holder 7 is positioned so as to locate the concave portion 12a of the lens holder portion 12 at a center of the dome viewed from the front face of FIG. 1 of the front face of the visual filed dome 15 (corresponds to an optical axis X of the correction lens), as shown in FIGS. 1 and 8. In such a state, the lens for correcting visibility (not shown) that is suitable for the visibility of the eye to be examined 19 is installed on and held by the concave portion 12a of the lens holder portion 12, and the axial portion 10b is moved and adjusted in the direction as shown by the arrows C and D of FIG. 8, fitting the visibility of the eye to be examined 19 and the lens for correcting the visibility is rotated in the concave portion 12a, referring to the angle index 12b in order to adjust its setting angle such that the eye to be examined 19 is able to clearly perceive the stimulus 16.

When the lens holder 7 is positioned at the set position P1, the top end 10d of the probe 10c is inserted in the inside of the lens holder sensor 13 as shown in FIG. 5 and the ON ("1") signal is outputted from the lens holder sensor 13. When the operation portion (not shown), such as a keyboard, instructs the perimeter 1 to start conducting perimetry on the eye to be examined 19 in the afore-mentioned state, the main controller 23 of the controller 24 presents the stimuli 16 at proper positions in the visual field dome 15 in order with a well-known method.

On this occasion, the main controller 23 gets the fixation state monitor 18 to monitor whether the eye to be examined 19 always fixates the fixation lamp 17 during the perimetry, that is, whether the fixation state is maintained in order to properly conduct the perimetry. But, the fixation state monitor 18 may not sufficiently monitor the fixation state of the eye to be examine 19 even with the LED illumination 20 that is a center portion driven at low brightness, that is different from a case where the lens holder 7 is at the stored position P2 since the lens holder 7 in which the lens for correcting the visibility is installed is located just before the eye to be examined 19 this time and shadows of the stem 11 of the lens holder 7, the lens holder portion 12 and the lens for correcting the visibility installed in the lens holder portion 12 are thrown on the front eye portion of the eye to be examined 19.

Then, the illumination controller 29 drives three LED illuminations 20, 21 and 22 so as to light the eye to be examined 19 that looks into the visual field dome 15 from the three portions, a central lower portion and lower portions on both sides of the center at a time when the lens holder sensor 13 outputs the ON "1" signal, that is, the lens holder 7 is positioned at the set position P1 in such a manner that the LED illumination 20 that is at the center portion is driven at high brightness (that is, a brighter state than such a time when the lens holder 7 was positioned at the stored position P2) and the LED illuminations 21, 22 at both sides are switched from a non-driving state to a driving state. By doing so, the eye to be examined 19 gets lights from the three directions that are different from each other and such lights operates so as to negate the shadows thrown by the stem 11 of the lens holder 7, the lens holder portion 12 and the lens for correcting the visibility on the front eye portion of the eye to be examined 19, so that the fixation state monitor 18 monitors the fixation state of the eye to be examined 19 in a good state.

Since all LED illuminations 20, 21 and 22 emit lights onto the eye to be examined 19 from the obliquely lower direction, the shadows of the lens for correcting the visibility and the lens holder portion 12 that are positioned at almost central position CT are extremely prevented from being projected onto the front eye portion that is on the optical axis Z of the lens for correcting the visibility and it is convenient. Since the LED illuminations 20, 21 and 22 are located on the lower side of the visual field dome 15, that is, on the lower hand of a perimetry position (corresponding to the center CT) in the visual field dome 15 of the eye to be examined 19, the illumination onto the eye to be examined 19 through the LED illuminations 20, 21 and 22 is not hindered by the forehead portion of the upper portion of the eye to be examined 19 and it is convenient. But, this does not prevent the LED illumination for lighting the eye to be examined 19 from being located on the upper side of the perimetry position of the eye to be examined 19 in the visual field dome 15.

Emitting light of illumination means to the eye to be examined 19 through the LED illuminations 20, 21 and 22 may be infrared light as well as visible light, and visible light and infrared light may be used together. The brightness of the respective LED illuminations 20, 21 and 22 is adjustable, and the brightness of the illumination onto the eye to be examined 19 can be also adjusted in such a manner that the illumination controller 29 automatically adjusts the brightness or an examiner manually adjusts the brightness according to a state of the eye to be examined 19 obtained through the fixation state monitor 18, such as a contrast of images of the eye to be examined 19 and a reflected state of Purkinje image. Furthermore, four LED illuminations may be located such that the brightness of the LED illumination that lights the eye to be examined 19 can be freely adjusted when the lens holder 7 is positioned at the set position P1.

In a case of the illumination means that is comprised of two or more light sources located at respectively different positions, such as the LED illuminations 20, 21 and 22, the illumination controller 29 controls to light the eye to be examined 19 through more light sources than a case where a visibility corrector, such as the lens holder 7, is positioned at the stored position P2 when such a visibility corrector is positioned at the set position P1, so that lighting is possible so as to cancel the shadows of the visibility corrector projected onto the front eye portion due to some light source by another light sources. Then, it is possible to light the eye to be examined 19 in a uniform state with little shadows and to more smoothly monitor the eye to be examined 19 through the fixation state monitor 18.

When the lens holder 7 is used at the set position P1, use of the lens holder 7, that is, use of the lens for correcting visibility at the time of perimetry is added to measurement data through the visual field judger 27 and the fixation state monitor 18 as attribution data based upon the output of the lens holder sensor 13.

Figure 10:
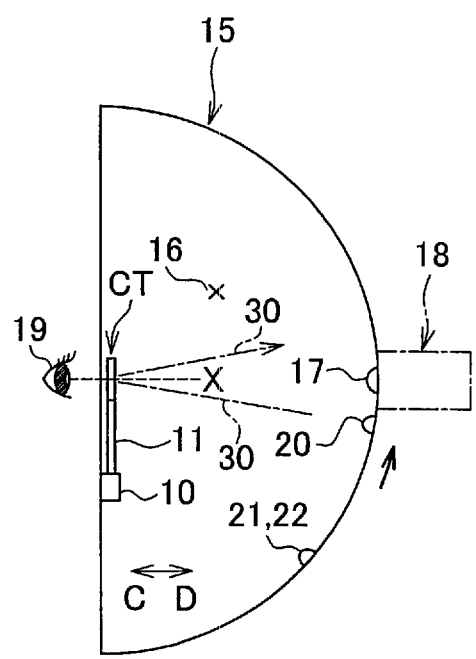
FIG. 10 is a side view that shows another example of the visual field dome.

Besides, the LED illumination 20 located on a lower hand of the fixation lamp 17 may be located on a side near the fixation lamp 17 as shown in FIG. 10, that is, near the central portion of the visual field dome 15 such that light 30 emitted from the LED illumination 20 can light the eye to be examined 19 via the lens for correcting visibility that is held by the lens holder portion 12 when the lens holder 7 is positioned at the set position P1. On this occasion, the light 30 from the LED illumination 20 is emitted onto the eye to be examined 19 via the lens for correcting visibility from the slightly obliquely lower direction rather than a horizontal direction as shown in FIG. 10. Even if a part of the light 30 from the LED illumination 20 reflects to the lens for correcting visibility, the reflected light 30 proceeds in a slightly obliquely upper direction and is prevented from being emitted directly to the fixation state monitor 18. Therefore, monitoring of the fixation state through the fixation state monitor 18 is not obstructed by the reflected light from the LED illumination 20.

At such a time, the LED illuminations 21 and 22 on the lower hand of FIG. 10 are able to light the eye to be examined 19 directly from a direction lower than the lens for correcting visibility held by the lens holder portion 12 without passing through the lens for correcting visibility, so that even if the shadows of the lens holder 7 and the lens for correcting visibility are projected onto the eye to be examined 19 through the LED illumination 20, the lighting is possible, canceling such shadows by the illumination from the lower direction through the LED illuminations 21 and 22.

The invention claimed is:

1. A perimeter having:
   a visual field measurer that measures a visual field of an eye to be examined when the eye to be examined perceives stimuli projected in order at different positions on a visual field dome:
   a fixation state monitor that monitors a fixation state of the eye to be examined at a time of perimetry;
   said fixation state monitor having two or more illuminators that light the eye to be examined at a brightness necessary for monitoring the fixation state of the eye to be examined; and
   a visibility corrector that corrects visibility of the eye to be examined; said perimeter further comprising:
      said visibility corrector having a stem being provided so as to set a starting position, return, rotate and move with a rotation axis that is located on an outside of said opening of said visual field dome as its center, and a lens holder portion being provided at a top end of the stem so as to be freely positioned between a set position of a center portion of said opening and a stored position provided at an outside of said opening in such a state that the stem and the lens holder portion are not watched from the opening by setting, returning rotating and moving of the stem;
      a position detector that detects whether said visibility corrector is positioned at said set position or said stored position;
      an illumination controller that respectively drives said two or more illuminators according to a position of said visibility corrector detected by said position detector.

2. The perimeter according to claim 1, wherein said illuminator is comprised of two or more light sources respectively located at different positions, and said illumination controller has means for driving said illuminators more than a case where said visibility corrector is positioned at said stored position when said visibility corrector is positioned at said set position.

3. The perimeter according to claim 1, wherein said illuminator has at least two light sources,
   at least one of said light sources is positioned at a position where the eye to be examined can be lighted via a lens for correcting visibility that is held by said visibility corrector when said visibility corrector is used at said set position;
   at least the other one light source is positioned at a position where the eye to be examined can be directly lighted without passing through said lens for correcting visibility that is held by said visibility corrector even if said visibility corrector is used at said set position.

4. The perimeter according to claim 1, wherein said illuminator has at least three light sources, and at least one of said light sources is located on a lower hand of a center of said visual field dome and at least two light sources are positioned at both sides of a lower hand of said visual field dome.

5. The perimeter according to claim 1, wherein said visibility corrector has a position detector that detects as to whether said lens holder portion is at said set position, further comprising memory means that records attribution data indicating use of said visibility corrector on measurement data by said fixation state monitor based upon signals from said position detector.

* * * * *